United States Patent [19]

Takano

[11] Patent Number: 4,604,113
[45] Date of Patent: Aug. 5, 1986

[54] DEODORIZING APPARATUS

[75] Inventor: Saburo Takano, Tokyo, Japan

[73] Assignee: Kabushiki Kaisha Sanai Estate, Tokyo, Japan

[21] Appl. No.: 545,854

[22] Filed: Oct. 27, 1983

[30] Foreign Application Priority Data

Oct. 27, 1982 [JP] Japan .................. 57-188128

[51] Int. Cl.[4] ................................ B01D 54/14
[52] U.S. Cl. ................................ 55/201; 55/203
[58] Field of Search ............... 55/90, 92, 184, 201, 55/203

[56] References Cited

U.S. PATENT DOCUMENTS

| 3,064,408 | 11/1962 | Erga et al. | 55/90 X |
| 3,960,524 | 6/1976 | Cumpston | 55/92 X |
| 3,989,485 | 11/1976 | Kilian | 55/90 |
| 4,008,056 | 2/1977 | Potter | 55/92 |
| 4,030,897 | 6/1977 | Pelzer et al. | 55/203 X |

Primary Examiner—Thomas Wyse
Attorney, Agent, or Firm—Fleit, Jacobson, Cohn & Price

[57] ABSTRACT

Deodorizing method and apparatus are disclosed herein which are characterized in that an offensive odor gas is blown or sucked into a deodorizing-swirling section consisting of a swirl-forming plate equipped with fixed wings which is provided in a hollow cylindrical body and a swirl-receiving member provided adjacent to the swirl-forming plate to be rotated in a swirl-like manner at a high speed so that a negative pressure is produced at the central portion of the swirl-forming plate; a deodorizing liquid is sucked and supplied into the deodorizing-swirling section by the negative pressure thus produced to cause the deodorizing liquid to be brought into mixing-contact with the offensive odor gas, while the deodorizing liquid and the offensive odor gas are being rotated in a swirl-like manner at a high speed, whereby the offensive odor gas is deodorized and the clean gas thus deodorized is discharged outside.

9 Claims, 4 Drawing Figures

DEODORIZING APPARATUS

BACKGROUND OF THE INVENTION (1) Field of the Invention

The present invention relates to a method of deodorizing an offensive odor gas and an apparatus used therefor.

(2) Description of the Invention

Offensive odors are emitted from a variety of sources. Such offensive odors, when exceed a certain concentration and are felt by a human organ of smell, lead to the so-called offensive odor pollution which has come into a social problem together with noises, so appropriate and prompt countermeasures for preventing and removing the offensive odors are strongly demanded as deodorizing treatment.

There have been heretofore various deodorizing methods, but they do not necessarily give satisfactory deodorizing effects. Some methods have such drawbacks that a considerable space is necessary for installation, and carrying and transferring are difficult due to the apparatus itself being complicated and large-sized; accordingly, timely installation is hardly possible to cope with the offensive odor-emitting sources. Further, they have the problems that the apparatus becomes expensive and are not easy to install; and its operation and handling need special technique and skill.

SUMMARY OF THE INVENTION

An object of the present invention is therefore to provide a method of deodorizing offensive odors and an apparatus used therefor which solve the above drawbacks encountered by the prior art.

According to one aspect of the invention, there is a provision of a deodrizing method in which an offensive odor gas is blown or sucked into a deodorizing-swirling section consisting of a swirl-forming plate equipped with fixed wings which is provided in a hollow cylindrical body and a swirl-receiving member provided adjacent to the swirl-forming plate to be rotated in a swirl-like manner at a high velocity so that a negative pressure is formed at the central portion of the swirl-forming plate; and a deodorizing liquid is sucked and supplied into the deodorizing-swirling section by the negative pressure to cause the deodorizing liquid to be brought into mixing-contact with the offensive odor gas while the deodorizing liquid and the offensive odor gas are being rotated in a swirl-like manner at a high velocity, whereby the offensive odor gas is deodorized and the clean gas thus deodorized is discharged to the outside.

According to another aspect of the invention, there is a provision of an apparatus used in the deodorizing method which apparatus comprises a deodorizing-swirling section consisting of a swirl-forming plate provided inside of a hollow cylindrical body at an appropriate position and equipped with a plurality of fixed wings each being spaced from one another and obliquely arranged and a frusto-conical swirl-receiving member provided adjacent to the swirl-forming plate, and a deodorizing liquid supply means one end of which is opened at the central portion of the swirl-forming plate and the other being communicated with a deodorizing liquid tank.

These and other objects, features and advantages of the invention will be well appreciated upon reading of the following description of the invention in conjunction with the accompanying drawings with understanding that modification, changes and variations will be easily made by the skilled in the art to which the invention pertains without departing from the spirit of the invention or the scope of the claims appended hereto.

BRIEF DESCRIPTION OF THE ACCOMPANYING DRAWINGS

DETAILED DESCRIPTION OF THE INVENTION

Figure 1:
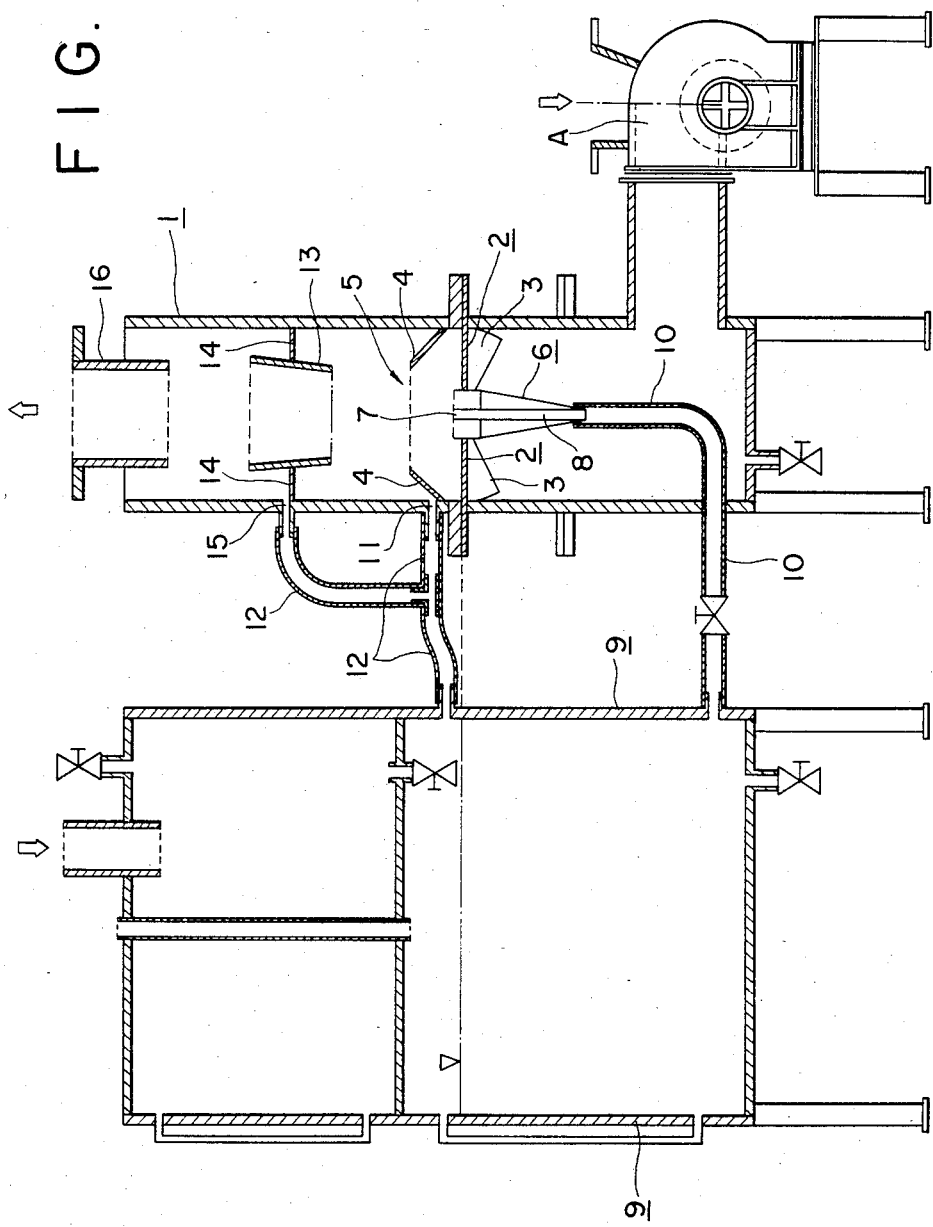
FIG. 1 is a sectional front view of an embodiment of a deodorizing apparatus according to the invention.

The invention will be now described below in greater detail with reference to the specific embodiment shown in the drawings which is merely illustrative of the invention and not to be interpreted to limit the scope thereof.

Reference numeral 1 is a hollow cylindrical body one end of which is opened and the other end being connected to a blower A.

Figure 3:
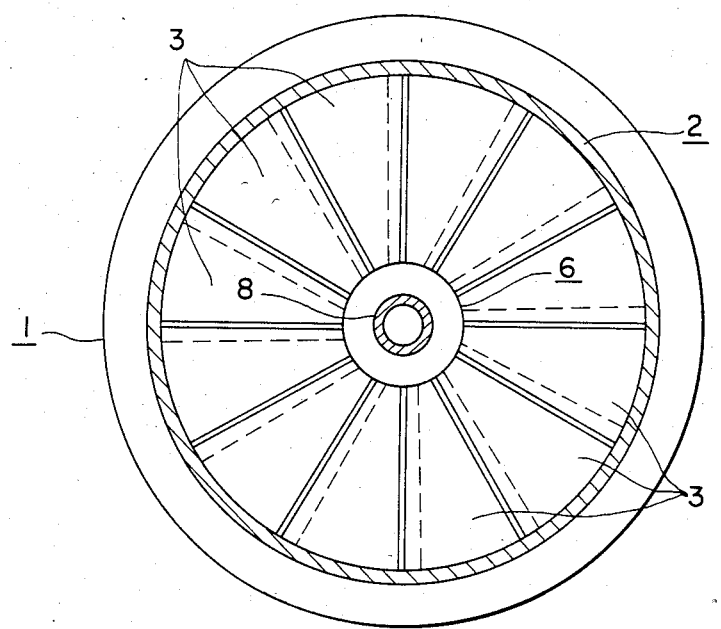
FIG. 3 is a plane view of a swirl-forming plate of the invention.
Figure 4:
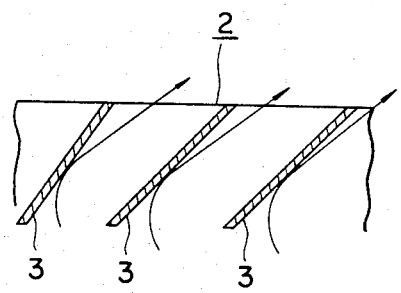
FIG. 4 is a sectional view illustrating the state in which the flow direction of an offensive odor gas is changed by fixed swings of the swirl-forming plate.

A swirl-forming plate 2 is transversely disposed within the hollow cylindrical body 1 in an appropriate position. The swirl-forming plate is equipped with twelve fixed wings or blades 3 which are spaced from one another and obliquely arranged in the hollow cylindrical body 1 while extending radially from the center portion toward the inner circumferential surface of the hollow cylindrical body in a wind-mill manner as shown in FIG. 3. The upper end faces of the fixed wings are almost flush with one another and the upper surface of the swirl-forming plate 2, as is clearly shown in FIG. 3.

As a matter of course, the number and inclination of the fixed wings 3 provided in a wind mill-like manner may be changed depending upon the inner diameter of the hollow cylindrical body 1, the flow rate of the offensive odor gas and the like.

A reference numeral 4 is a swirl-receiving member in a frusto-conical shape which is projectingly provided in the inner circumference of the hollow cylindrical body and adjacent to and upward of the swirl-forming plate 2 provided within the hollow cylindrical body. The diameter of the lower side of the swirl-receiving member is designed larger than the diameter of the upper side. A reference numeral 5 is a deodorizing-swirling section constituted by the swirl-forming plate 2 provided in the hollow cylindrical body 1 and the swirl-receiving member 4 provided adjacent to the swirl-forming plate 2.

A deodorizing liquid supply means 6 is formed in an inverse frusto-conical shape and is fitted and secured to the central portion of the swirl-forming plate. The upper end of the deodorizing liquid supply means 6 is opened at 7 projecting slightly upward from the swirl-forming plate 2, while the lower end portion is projected in an inverse frusto-conical shape downward from the swirl-forming plate 2.

Within the deodorizing liquid supply means 6 is vertically provided a small-diameter tube 8 penetrating therethrough, while to the downside of the deodorizing liquid supply means 6 is connected a deodorizing liquid supply tube 10 one end of which is extended penetrating the hollow cylindrical body 1 to the outside thereof and the other end being integrally communicated to the deodorizing liquid supply means 6. Thus, the deodorizing liquid is supplied into the deodorizing liquid supply means 6 in the hollow cylindrical body 1 via the liquid supply tube 10.

As shown in FIG. 1, if the upper face of the deodorizing liquid in the deodorizing liquid tank 9 is made on the same level as the upper end face of the deodorizing liquid supply means 6 in the hollow cylindrical body 1, the deodorizing liquid is spontaneously supplied up to the upper end face of the deodorizing liquid supply means 6.

Next, the manner in which the offensive odor gas is deodorized by using the apparatus according to the invention will be explained below.

The offensive odor gas emitted from the offensive odor emission source is sucked and blown into the hollow cylindrical body 1 from the lower side thereof by means of the blower A. Then, the offensive odor gas goes straight in an upper direction, i.e., in an axial direction of the hollow cylindrical body, and passes through the twelve wings 3 of the swirl-forming plate 2 provided midway of the hollow cylindrical body 1 while spaced from one another and obliquely arranged in a wind mill-like manner, so that it is blown upward in an oblique direction, while its flow direction is changed, that is, it is rotated in a swirl form along the inner circumferential surface of the hollow cylindrical body 1 and the swirl-receiving member 4 at a high speed while being in contact therewith. Thereby, the swirl of the gas is formed at a high velocity at the deodorizing-swirling section 5.

In this case, the offensive odor gas rotating in a high velocity on or over the swirl-forming plate 2 becomes a swirl which flows fastest in an inner circumferential direction of the hollow cylindrical body 1. Consequently, the swirl central portion of the offensive odor gas is formed at the central portion of the swirl-forming plate 2, so the pressure drops upward of the central portion of the swirl-forming plate 2 to form a negative pressure portion therein. As the offensive odor gas is rotated at a high speed, the deodorizing liquid is sucked up to and flow from the opening 7 of the deodorizing liquid supply means by the negative pressure which is opened at the central portion of the swirl-forming plate, so that the deodorizing liquid flows over the swirl-forming plate 2 and stays on the upper faces of the twelve wings of the swirl-forming plate 2. As the offensive odor gas swirls at a high speed, the deodorizing liquid staying on the upper faces of the wings 3 of the swirl-forming plate 2 is flown rotating at a relatively high velocity on the upper faces of the wings by the action of the offensive odor gas swirl. Thus, a thin film of the swirling deodorizing liquid is formed onto the upper faces of the wings.

The offensive odor in the gas is then deodorized through mixing-contact between the film-like deodorizing liquid and the offensive odor gas in the rotating state.

The mixing-contact between the offensive odor gas and the deodorizing liquid is effectively carried out on the wings of the swirl-forming plate 2 and further within the deodorizing-swirling section 5 between the swirl-forming plate and the swirl-receiving member 4. At that time, since the swirl speed of the offensive odor gas rotating at a high velocity differs from that of the swirling deodorizing liquid in a flim-like form, the mixing-contact therebetween is thoroughly done, and at the same time the deodorizing liquid is fully atomized and mixed into the offensive odor gas by the action of the offensive odor gas blowing out through the spaces between the wings 3, so that the deodorizing effect can be further enhanced.

As the deodorizing liquid used in the invention, there may be appropriately selected the conventional liquid neutralizing agent, oxidizing agent, decomposing agent, absorbent or the like depending on the kind of the offensive odor.

In addition, since the lower end portion of the deodorizing liquid supply means 6 is projected in an inverse frusto-conical shape downward of the swirl-forming plate 2, the offensive odor gas otherwise going up straight changes its flow direction along the deodorizing liquid supply means 6, so that the offensive odor gas is blown upward more effectively from the spaces between the obliquely fixed wings 3.

Figure 2:
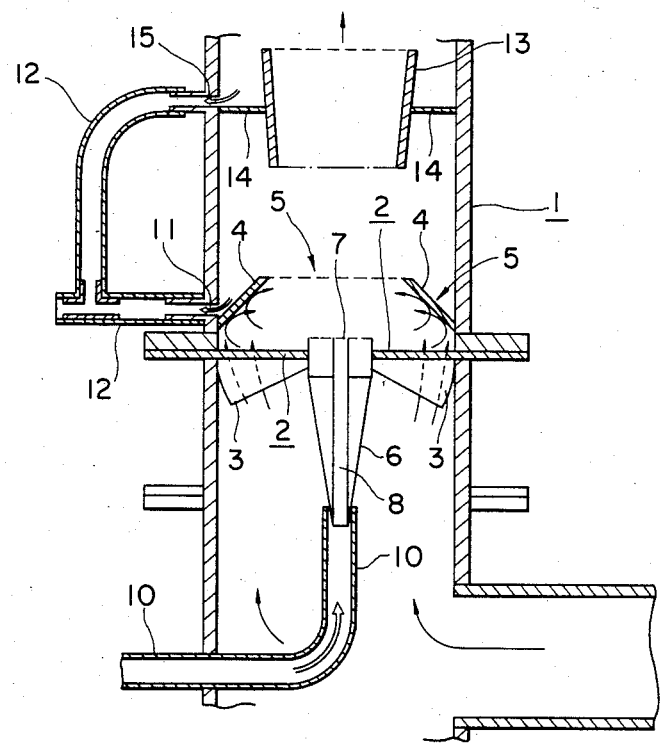
FIG. 2 is a sectional view of a part of the apparatus of the invention.

In FIG. 2, a reference numeral 11 is an outlet for discharging the deodorizing liquid which is bored at a portion of the hollow cylindrical body 1 adjacent to the upper side face of the swirl-receiving member 4. Since the deodorizing liquid discharge outlet 11 is bored in the cylindrical hollow body 1 near the upper side face of the swirl-receiving member 4 in the above manner, the deodorizing liquid overflowing on the upper side of the swirl-receiving member 4 together with the deodorized gas swirl rotating at a high velocity is almost completely separated from the gas because the swirling speeds of the gas and the deodorizing liquid rapidly drop on the upper side of the swirl-receiving member 4, whereby the deodorizing liquid stays on the upper side face of the swirl-receiving member 4 and is discharged outward from the deodorizing liquid discharge outlet 11 successively.

According to the invention, there is obtained the advantage that the deodorizing liquid discharged from the outlet 11 is circulated into the deodorizing liquid tank 9 through a circulation pipe 12.

In FIGS. 1 and 2, a reference numeral 13 is a gas discharge cylindrical member in an inversely tapered shape with the diameter of the lower end portion being smaller, which member is fitted and secured to the central portion of a partition wall 14 stretched at a right angle within the hollow cylindrical body 1 upward of the swirl-receiving member 4, while penetrating the partition wall.

Since the gas discharge cylindrical member 13 with the lower end portion of a smaller diameter is provided in the hollow cylindrical body upward of the swirl-receiving member 4 as mentioned above, the deodorized gas and deodorizing liquid as mixed can be completely separated from each other with decrease in the swirl velocity. Accordingly, the deodorized gas including substantially no deodorizing liquid is discharged from the gas discharge cylindrical member 13.

A reference numeral 15 is a deodorizing liquid discharge outlet which is bored at a portion of the hollow cylindrical body 1 to be communicated with the upper side face of the partition wall. The deodorizing liquid flown out upwardly from the gas discharge cylindrical member 13 is discharged from this deodorizing liquid discharge outlet 15 to the outside of the hollow cylindrical body 1 to be circulated to the deodorizing liquid tank 9 through the circulation pipe 12.

A gas discharge cylinder 16 is formed in a diameter smaller than that of the hollow cylindrical body 1 and integrally provided on the upper end of the hollow cylindrical body 1.

By partitioning the space within the hollow cylindrical body over the swirl-receiving member 4 into parts, the invention has another advantage that with the deodorized gas swirl decelerated, the deodorizing liquid entrained in the gas swirl is fully separated, so that the gas discharged from the gas discharge cylinder 16 is a clean gas including neither offensive odor nor deodorizing liquid.

Further, since the upper faces of the fixed wings 3 of the swirl-forming palte 2 are almost flush with one another, the invention has a still another advantage that the deodorizing liquid sucked and flown out onto the swirl-forming plate 2 due to the offensive odor gas swirl rotating at a high speed along the swirl-forming plate 2 becomes a film thereon to be smoothly flown as a swirl at a high speed.

Accordingly to the invention, the deodorant is a liquid and the deodorizing is carried out at the deodorizing-swirling section 5, while the film-like swirling deodorizing liquid and the atomized deodorizing liquid are mixed and contacted with the offensive odor gas. Thus, even when particulate matters are included in the offensive odor gas, a dust-removal effect can be obtained, so that an extremely effective dust removal as well as deodorizing can be both performed.

If a poisonous gas such as sulphurous acid gas is contained in the offensive odor gas, the invention has the advantage that the desulfunizing and poison removal can be done by mixing a desulfurizing agent with the deodorizing liquid, thereby avoiding the pollution.

When the hollow cylindrical body 1, the swirl-forming plate 2, the swirl-receiving member 4 and the deodorizing liquid supply means 6 are made of transparent tempered glass, transparent synthetic resin or the like, the state in which the deodorizing liquid and the offensive odor gas are mixed and contacted with each other while rotated at a high speed in a swirl form can be observed from the outside of the hollow cylindrical body 1.

As shown in FIG. 1, according to the deodorizing apparatus of the invention, the deodorizing is carried out by blowing the offensive odor gas by the blower A connected to the lower portion of the hollow cylindrical body. Alternatively, with the blower A removed from the downside of the hollow cylindrical body 1 and this downside opened, the offensive odor gas may be strongly sucked into the hollow cylindrical body from the upper portion thereof by an appropriate means for deodorization.

The deodorizing effect when the apparatus according to the invention was employed are as follows:

EXAMPLE 1

Kind of the offensive odor: triethylamine.
Installed site: Isocure (Mold-forming method for casting); Gas neutralization discharge outlet.
Measuring method: Detector-tube system.
Use conditions of apparatus of the invention: Blow amount 12 m$^3$/min. Applied voltage 100 V.
Deodorizing liquid: Deodorizing liquid *OLT-A (tradename) which may be replaced by appropriate deodorizing liquid commercially available.
*OLT-A: wood vinegar containing Fe$^{++}$ and Fe$^{+++}$ metal ions.

| Repetition No. of measurement | 1 | 2 | 3 | 4 | 5 | 6 |
|---|---|---|---|---|---|---|
| At neutralization discharge outlet (p.p.m.) | 0.02 | 0.04 | 0.02 | 0.024 | 0.02 | 0.03 |
| Discharge outlet of the invention apparatus (p.p.m.) | 0.00 | 0.00 | 0.00 | 0.00 | 0.00 | 0.00 |

EXAMPLE 2

Kind of the offensive odor: ammonia.
Installed site: Air-tight chamber of 120 m$^3$.
Measuring method: Detector-tube system.
Used conditions of apparatus of the invention: Blow amount 120 m$^3$/min. Applied voltage 100 V.
Deodorizing liquid: Deodorizing liquid OLT-A (tradename) which may be replaced by appropriate deodorizing liquid commercially available.

| Lapse time (min.) | 0 | 3 | 6 | 9 | 12 | 15 | 20 | 25 |
|---|---|---|---|---|---|---|---|---|
| Measured value (p.p.m.) | 43 | 12 | 4 | 1.5 | 0.9 | 0.5 | 0.08 | 0.00 |

Quite different from the conventional method of the shower system in which the deodorizing is carried out through the gas-liquid contact between the deodorizing liquid and the offensive odor gas, according to the present invention, the deodorizing liquid is rotated in a swirl form at a high speed together with the offensive odor gas, so that the film of the deodorizing liquid is formed and stirred for the mixing-contact by the offensive odor gas itself and therefore the gas-liquid contact "gas⇌liquid" is thoroughly effected. Thus, the deodorizing effect can be considerably enhanced.

Since the contact-mixing between the deodorizing liquid and the offensive odor gas is ideally and fully carried out, the invention has the advantage that the particulate dust contained in the offensive odor gas can be simultaneously removed.

Further, since the hollow cylindrical body 1 is partitioned into plural parts, the invention has further the advantage that substantially no water is entrained in the deodorized gas to be discharged.

In addition, since the apparatus according to the invention can be small-sized, it is easy to carry. Moreover, because of its simple structure, it needs neither special technique nor skill in operating and handling, so that every one can use it without difficulty.

Furthermore, no great space is required for the installation due to the small-sized apparatus, and it can be installed with easy and at low cost in the vicinity of the offensive odor-generating sources without necessitating a large space for installation. Besides, since the deodorizing liquid is supplied from and circulated into the deodorizing liquid tank 9 provided outside of the hollow cylindrical body 1, the invention has the advantage that an appropriate deodorizing liquid may be selected depending on the offensive odor kinds.

What is claimed is:

1. A deodorizing apparatus, comprising a hollow cylindrical body, a deodorizing-swirling section comprising a swirl-forming plate which is transversely arranged inside of the hollow cylindrical body and is equipped with a plurality of fixed blades each being spaced from one another and radially and obliquely arranged, and a frusto-conical swirl-receiving member provided adjacent to the swirl-forming plate inside of the hollow cylindrical body and having a discharge opening in a side thereof remote from a side thereof adjacent the swirl-forming plate, a deodorizing liquid supply means having one open end opening at a central portion of the swirl-forming plate into the deodorizing-swirling section, a deodorizing liquid tank to which is connected an opposite end of the deodorizing liquid supply means, and means for forcibly feeding a gas to be deodorized into the deodorizing-swirling section in an axial direction of the hollow cylindrical body, such that the fed gas is swirled by the action of the radially and obliquely arranged blades, and the deodorizing liquid is fed through said open end of the deodorizing liquid supply means from the deodorizing liquid tank by a sucking action of the swirled gas, thereby bringing the deodorizing liquid into contact with the gas to be deodorized and performing the deodorization of the gas.

2. The deodorizing apparatus as claimed in claim 1, wherein end faces of the fixed blades of the swirl-forming plate are substantially flush with respect to one another and a surface of the swirl-forming plate, such that the blades form a film of the deodorizing liquid on the end faces of the blades and the plate surface.

3. The deodorizing apparatus as claimed in claim 1, wherein a partition wall is provided adjacent the discharge opening in the swirl-receiving member and within the hollow cylindrical body, and an essentially cylindrical tube for discharging the deodorized gas is provided at the central portion of the partition wall.

4. The deodorizing apparatus as claimed in claim 3, wherein first and second outlets, for discharging the deodorizing liquid, are provided in the hollow cylindrical body adjacent to the swirl-receiving member and the partition wall, respectively.

5. The deodorizing apparatus as claimed in claim 3, wherein an essentially cylindrical member, for discharging the deodorized gas, is mounted in the hollow cylindrical body adjacent the partition wall and the essentially cylindrical gas-discharge tube.

6. The deodorizing apparatus as claimed in claim 1, wherein the hollow cylindrical body, the swirl-forming plate, the swirl-receiving member and the deodorizing liquid supply means are made of a transparent material.

7. The deodorizing apparatus as claimed in claim 1, wherein the swirl-forming plate creates a negative pressure in the hollow cylindrical body adjacent the plate, to suck the deodorizing liquid through the deodorizing liquid supply means into the deodorizing-swirling section.

8. The deodorizing apparatus as claimed in claim 1, wherein the swirl-forming plate and the frusto-conical swirl-receiving member cause the gas being deodorized, and the deodorizing liquid, to swirl at different speeds, to enhance mixing thereof.

9. The deodorizing apparatus as claimed in claim 1, wherein the open end of the deodorizing supply means includes a tube which feeds through an open-ended inversely frusto-conical member secured to a central portion of the swirl-forming plate.

* * * * *